US009464891B2

(12) United States Patent
Zeng et al.

(10) Patent No.: US 9,464,891 B2
(45) Date of Patent: Oct. 11, 2016

(54) METHOD FOR MEASURING THICKNESS BY PULSED INFRARED THERMAL WAVE TECHNOLOGY

(75) Inventors: Zhi Zeng, Beijing (CN); Xun Wang, Beijing (CN); Ning Tao, Beijing (CN); Lichun Feng, Beijing (CN); Cunlin Zhang, Beijing (CN)

(73) Assignees: CAPITAL NORMAL UNIVERSITY, Beijing (CN); BEIJING WAITEKSIN ADVANCED TECHNOLOGY CO., LTD., Beijing (CN); CHONGQING NORMAL UNIVERSITY, Chongqing (CN)

( * ) Notice: Subject to any disclaimer, the term of this patent is extended or adjusted under 35 U.S.C. 154(b) by 341 days.

(21) Appl. No.: 14/002,022

(22) PCT Filed: Jun. 14, 2011

(86) PCT No.: PCT/CN2011/000984
§ 371 (c)(1),
(2), (4) Date: Feb. 4, 2014

(87) PCT Pub. No.: WO2012/167403
PCT Pub. Date: Dec. 13, 2012

(65) Prior Publication Data
US 2014/0153608 A1    Jun. 5, 2014

(30) Foreign Application Priority Data
Jun. 9, 2011   (CN) .......................... 2011 1 0154204

(51) Int. Cl.
*G01B 21/08*    (2006.01)
*G01N 25/72*    (2006.01)

(52) U.S. Cl.
CPC ............. *G01B 21/085* (2013.01); *G01N 25/72* (2013.01)

(58) Field of Classification Search
CPC ..... G01B 21/085; G01N 25/72; G01N 25/18
USPC ....................................................... 374/5, 7
See application file for complete search history.

(56) References Cited

U.S. PATENT DOCUMENTS 5,444,241 A * 8/1995 Del Grande ............ G01N 25/72
250/253
5,711,603 A 1/1998 Ringermacher et al.
(Continued)

FOREIGN PATENT DOCUMENTS

CA    2546524 A1    11/2006
CN    1696674 A     11/2005
(Continued)

OTHER PUBLICATIONS

International Search Report (ISR), PCT/CN2011/000984, Mar. 22, 2012 (8 PAGES).
(Continued)

*Primary Examiner* — Lisa Caputo
*Assistant Examiner* — Philip Cotey
(74) *Attorney, Agent, or Firm* — Rankin, Hill & Clark LLP

(57) ABSTRACT

A method for measuring thickness or defect depth by pulsed infrared thermal wave technology is described. The method includes heating a measured object by pulsed heating devices, and at the same time, obtaining a thermal image sequence on the surface of the measured object by an infrared thermography device, and storing the thermal image sequence in a general-purpose memory. The method also includes multiplying a temperature-time curve at every point of the thermal image sequence by a corresponding time, thereby obtaining a new curve. The method also includes calculating a first-order differential and obtaining a peak time thereof. The method also includes use of one or more formulas to thereby determine the thickness or the defect depth of the measured object.

4 Claims, 3 Drawing Sheets

(56) References Cited

U.S. PATENT DOCUMENTS

| | | | |
|---|---|---|---|
| 6,394,646 B1* | 5/2002 | Ringermacher | G01B 11/06 250/330 |
| 6,542,849 B2 | 4/2003 | Sun | |
| 7,365,330 B1 | 4/2008 | Sun | |
| 7,409,313 B2 | 8/2008 | Ringermacher et al. | |
| 7,419,298 B2 | 9/2008 | Ouyang et al. | |
| 2002/0110176 A1* | 8/2002 | Sun | G01N 25/72 374/5 |
| 2002/0126730 A1* | 9/2002 | Sun | G01N 25/72 374/43 |
| 2002/0128797 A1 | 9/2002 | Sun | |
| 2002/0134817 A1* | 9/2002 | Shepard | G01N 25/72 228/105 |
| 2003/0193987 A1* | 10/2003 | Zalameda | G01J 5/62 374/5 |
| 2004/0028113 A1* | 2/2004 | Schlagheck | G01N 25/72 374/57 |
| 2005/0018748 A1* | 1/2005 | Ringermacher | G01N 25/72 374/121 |
| 2006/0062561 A1* | 3/2006 | Shepard | G03B 41/00 396/155 |
| 2007/0036199 A1 | 2/2007 | Ouyang et al. | |
| 2007/0143061 A1 | 6/2007 | Ringermacher et al. | |
| 2007/0146512 A1* | 6/2007 | Suzuki | H04N 5/332 348/272 |
| 2008/0111078 A1 | 5/2008 | Sun | |
| 2008/0137105 A1* | 6/2008 | Howard | G01N 25/72 356/630 |
| 2009/0245321 A1* | 10/2009 | Ringermacher | G01N 25/72 374/5 |
| 2010/0074515 A1* | 3/2010 | Zhao | G01N 25/72 382/149 |
| 2010/0100275 A1* | 4/2010 | Mian | G01M 17/013 701/31.4 |

FOREIGN PATENT DOCUMENTS

| | | |
|---|---|---|
| CN | 1869581 A | 11/2006 |
| CN | 101055169 A | 10/2007 |
| CN | 1696674 B | 6/2010 |
| EP | 1726943 A1 | 11/2006 |
| EP | 1798517 A1 | 6/2007 |
| JP | 2006329982 A | 12/2006 |
| JP | 2007178429 A | 7/2007 |
| KR | 20060121677 A | 11/2006 |
| RU | 2431823 C2 | 10/2011 |
| SG | 127835 A1 | 12/2006 |

OTHER PUBLICATIONS

Liu, Bo et al; Depth Measure and Edge Detection of Defect Based on Infrared Thermal Wave Nondestructive Testing; Journal of Capital Normal University (Natural Science Edition); Oct. 2006, vol. 27, No. 5, pp. 22-25 (Chinese Language).

Wang, Yan et al; Infrared Thermal Wave Testing on the Lamination Defect of Glass Fiber Composite Material. Nondestructive Testing; 2010; vol. 32, No. 11, pp. 880-883 (Chinese Language).

Zhang, Xiao Chuan et al; Measurement of Thickness of Glass Fiber Reinforced Plastic Flat Bottom Hole Sample by Infrared Thermal NDT. Laser & Infrared. Jan. 2006; vol. 36, No. 1, pp. 16-18 (Chinese Language).

* cited by examiner

METHOD FOR MEASURING THICKNESS BY PULSED INFRARED THERMAL WAVE TECHNOLOGY

CROSS REFERENCES TO RELATED APPLICATIONS

This application is a national stage application and claims priority from International Application serial No. PCT/CN2011/000984 filed on Jun. 14, 2011.

TECHNICAL FIELD

The present subject matter relates to the field of nondestructive inspection testing technology, more particularly to infrared thermal wave technology and a method for measuring thickness or defect depth of measured objects by using pulsed infrared thermal wave technology.

BACKGROUND

A nondestructive testing method using pulsed infrared thermal waves is a nondestructive testing technology developed since the 1980s. Based on thermal wave theory as a theoretical basis, the nondestructive testing method using pulsed infrared thermal waves achieves quantitative diagnosis of internal defects or damage of an object, by actively applying pulsed thermal excitation to a measured object, continuously observing and recording object surface temperature field variation with an infrared thermal imaging system, and by testing, acquiring, data processing and analyzing time series thermal wave signals according to modern computer technology and image information processing technology.

An important application of quantitative measurement of nondestructive testing technology by using pulsed infrared thermal waves is to measure defect depth or thickness of a measured object. The defect depth or the measured object thickness is generally calculated by obtaining a certain characteristic time constant of a temperature-time curve. U.S. Pat. No. 5,711,603 uses a derivative peak time of a defect region subtracting a reference region temperature curve as the characteristic time. U.S. Pat. No. 5,711,603 requires that a reference region is first selected, which is difficult to achieve in some applications and introduces errors. A thermal contrast peak method uses the peak time of the defect region subtracting a reference region temperature curve as the characteristic time. However, the peak time is highly affected by factors such as defect size and so on, and also requires a reference region. S. M. Shepard uses the second-order peak time of a temperature-time logarithmic curve as the characteristic time. The method of S. M. Shepard has an advantage that the corresponding peak time is at a relatively early time and is less affected by three-dimensional thermal diffusion. However, the method of S. M. Shepard has a drawback that the second-order differential peak time is largely affected by noise. In the above noted several methods, the defect depth or thickness and the obtained corresponding characteristic time value have determined theoretical relational expressions. A logarithmic deviation time method uses a separation time of the defect region and non-defect region in a temperature-time logarithmic curve as the characteristic time. The logarithmic separation point method also requires a reference curve, and at the same time, it is relatively difficult to accurately determine the separation point. U.S. Pat. No. 6,542,849 selects an approximately linear region from a temperature-time curve, which is fitted to derive its slope. And then defect depth is finally derived by curve fitting with a temperature decreasing theoretical formula. X. Maldague performs a Fourier transform to temperature-time curves, subtracts a reference curve, and uses the zero value time as the characteristic time value.

The above noted several methods in the prior art require a reference curve or a second-order differentiation. Each method has its own different application area.

SUMMARY

Aiming at the technological problem that the above methods require a reference curve or require performing a second-order differentiation, the present subject matter provides a new method for thickness measurement using pulsed infrared thermal wave technology to measure the thickness or the defect depth of objects to be measured (referred to herein as the "measured objects").

In order to solve the technological problems described above, a method of the present subject matter for measuring the thickness or the defect depth using pulsed infrared thermal wave technology comprises the following steps or operations:

(1) Heating a measured object by a pulsed heating device, at the same time, obtaining a thermal image sequence on the surface of the measured object by an infrared thermal imager, and storing the thermal image sequence in a general-purpose memory;

(2) Multiplying a temperature-time curve of each pixel in the thermal image sequence by $\sqrt{t}$ of a corresponding time t, thereby obtaining a new curve f;

(3) Calculating a first-order differential for the f to obtain a f' and obtaining a peak time $t_{apst}$ of the f';

(4) Calculating L by a formula $$t_{apst} = \frac{L^2}{2\alpha},$$

wherein $\alpha$ is a thermal diffusivity coefficient, and L is the measured object thickness or the defect depth.

In this method, the thermal diffusivity coefficient $\alpha$ is known.

In applications in which the thermal diffusivity coefficient $\alpha$ is unknown, a sample which has the same material property with the actual measured object and which has a known L is selected as a standard sample. The standard sample is measured to obtain a linear relationship between $t_{apst}$ and $L^2$. L is obtained according to the above said linear relationship and the value $t_{apst}$ of the measured object.

The pulsed heating device can be in the form of high-energy flash lamps or other pulsed heat sources.

By the above technological solution, the present subject matter can measure the measured object thickness or the defect depth without a reference curve and only with a first-order differential. And thus the present processing method becomes simpler than previously known methods.

Figure 1:
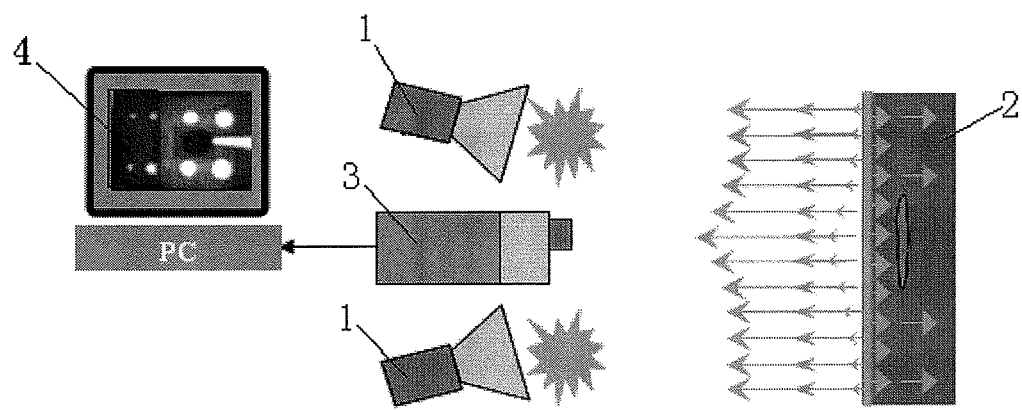
FIG. 1 is a schematic diagram of pulsed infrared thermal wave technology.

The following is a description of reference signs used in the noted figures: High-energy flash lamps—1; a measured object—2; an infrared thermal imager—3; and a computer—4.

DETAILED DESCRIPTION OF THE EMBODIMENTS

The shape, structure, and characteristics of the present subject matter may be better understood from the following detailed description of various embodiments illustrated in the accompanying drawings.

The theoretical basis of the present subject matter is on the solution of a one-dimensional heat conduction equation based on pulsed plane heat source excitation. And with regard to the semi-infinite homogeneous medium, under an irradiation of uniform pulsed heat source parallel to a medium plane, the heat conduction equation can be simplified as:

$$k\frac{\partial^2 T(x,t)}{\partial x^2} - \rho c \frac{\partial T(x,t)}{\partial t} = -q\delta(t)\delta(x)\bigg|_{\substack{x=0\\t=0}} \quad (1)$$

In equation (1), T(x,t) is the temperature at the position x and at the time t, $q\delta(t)\delta(x)$ is a pulsed heat source function, q is a constant and q is the amount of heat applied per unit area, and k (W/m·K) is the thermal conductivity. The product of the density ρ (kg/m³) and specific heat c is the heat capacity of the medium material. The thermal diffusivity coefficient is α=k/(ρc). For a particular medium, under general circumstances, α can be regarded as a constant.

When there is a defect under the object surface, or when the measured object is relatively thin, the solution of the heat conduction equation is:

$$\Delta T(0,t) = \frac{q}{w\sqrt{\pi t}}\left[1 + 2\sum_{n=1}^{\infty} \exp\left(\frac{-n^2 L^2}{\alpha t}\right)\right] \quad (2)$$

In equation (2), e is the thermal effusivity of the measured object, n is an n-th reflection which occurs when a pulse propagates to the interface between two materials, and L is the thickness (or the defect depth) of the measured object. Both ends of the above said formula multiplies √t of the corresponding time. And thus a new variable f is defined as:

$$f(t) = \Delta T(0,t) \cdot \sqrt{t} = \frac{q}{e\sqrt{\pi}}\left[1 + 2\sum_{n=1}^{\infty} \exp\left(\frac{-n^2 L^2}{\alpha t}\right)\right] \quad (3)$$

Next, the derivative of formula (3) is taken to obtain a f'(t) curve. Considering multiple reflections, the peak time of the f'(t) curve can be approximately expressed as:

$$t_{apst} = \frac{L^2}{2\alpha} \quad (4)$$

Thereby the theoretical relationship between the defect depth or the thickness of the measured object and the peak time of the first-order differentiation of f is obtained. The defect depth or the measured object thickness L can be obtained by the peak time of the first-order differentiation of f. In terms of the infrared thermal wave theory, the measured value L is the first interface encountered by a thermal wave in a heat conduction process. That is, the measured value L is the defect depth. And if there is no defect, the measured value L is the thickness.

The theoretical basis of the present subject matter is based on a pulsed thermal imaging method. Assuming that the ideal pulsed heat source irradiates at the surface (x=0) of the measured object at the time t=0, the energy irradiated is completely absorbed by the surface. In an actual system, the heating device for heating the measured object can be a high-energy flash lamp or other pulse-type heating devices. In order to improve the calculation accuracy, it should be ensured that an irradiating time of the pulsed flash lamp should be short enough, and that an acquisition frequency of the thermal imaging system should be configured higher. An acquisition time is set up according to material properties of the specific measured object.

FIG. 1 is a technological schematic diagram illustrating pulsed infrared thermal wave technology for measuring the defect depth or the thickness of the measured object in accordance with the present subject matter. And at the same time, FIG. 1 is also a schematic illustration of a typical structure of an actual system using the method of the present subject matter.

Referring to FIG. 1, a plurality of high-energy flash lamps apply a visible light energy to the surface of the measured object 2. The temperature of the surface of the measured object 2 increased by the energy of the high-energy flash lamps 1, and instantaneously arrives at a peak value. And due to a temperature difference between the surface and the interior of the measured object 2, heat is transmitted from the surface to the interior of the object along the direction of the depth. An infrared thermal imager 3 records the change in the temperature field of the surface of the measured object 2 in real time. A computer 4 acquires thermal image data from the infrared thermal imager 3, and obtains a thermal image sequence on the temperature field of the surface of the measured object 2.

The process of using the pulsed thermal imaging method for measuring the defect depth or the measured object thickness will be described combined with the following embodiment. This embodiment uses an actual measured object which is manufactured after an aluminum material is surface anodized. In the actual measured object, there are 6 wedge-shaped grooves having a depth of 2 to 7 mm from the surface.

Figure 2:
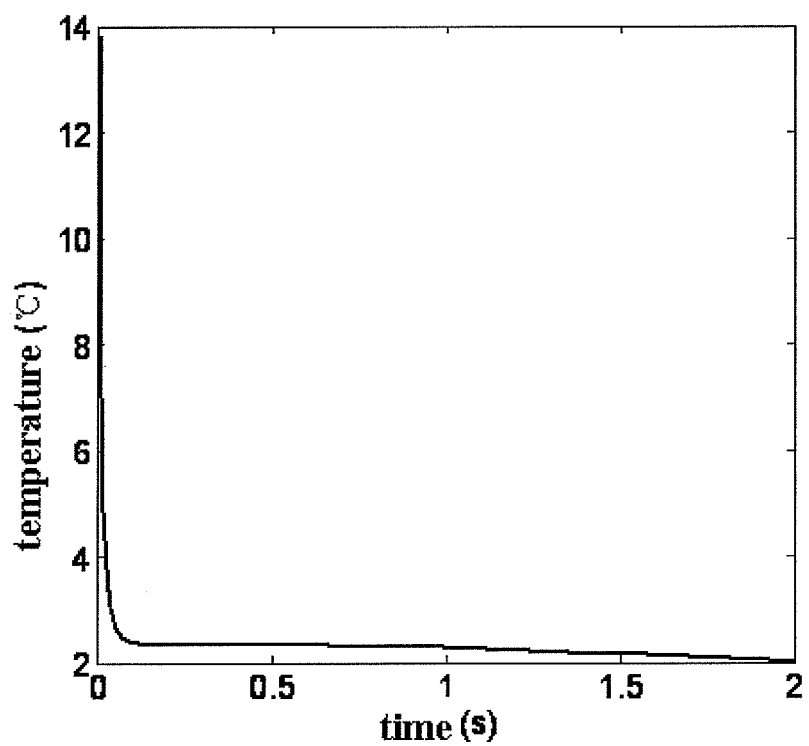
FIG. 2 is a typical temperature decreasing curve of pulsed infrared thermal wave.
Figure 3:
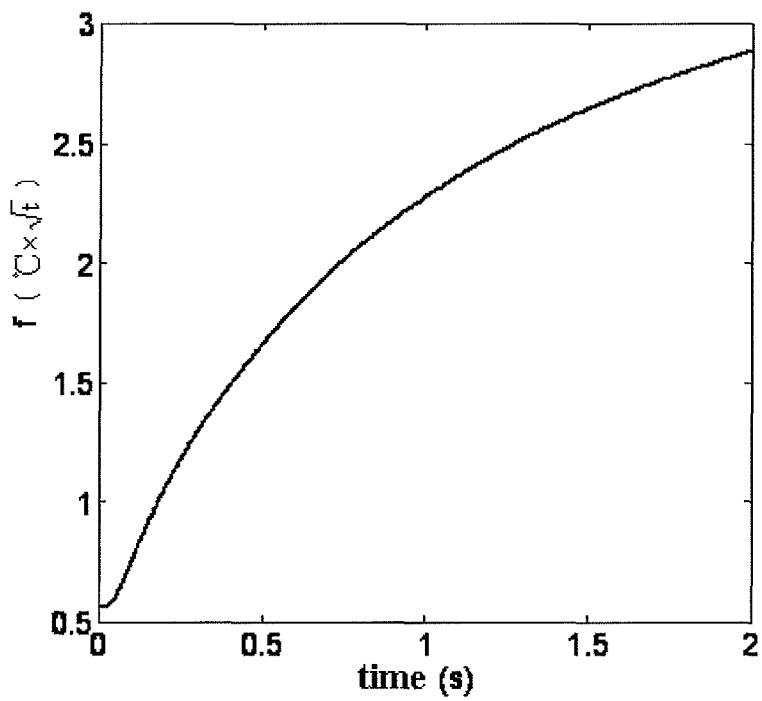
FIG. 3 is a curve of the variable f obtained after the curve of FIG. 2 is processed.

FIG. 2 is a temperature decreasing curve, i.e. a temperature-time curve, of a surface corresponding to a wedge-shaped groove with a certain depth in the obtained thermal image sequence after the above actual measured object is measured employing the system of FIG. 1. A f curve shown in FIG. 3 is obtained by processing the temperature decreasing curve by the formula (3). The f curve obtained by processing the original temperature decreasing curve is a temperature rising curve. The f curves corresponding to materials with different attributes or corresponding to structures with different depths have different change rates and different saturation rates.

Figure 4:
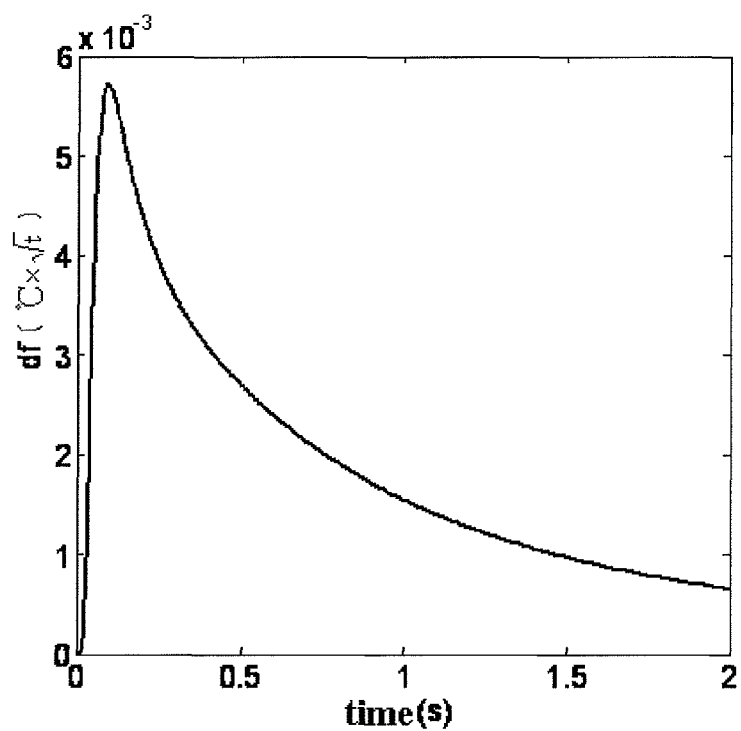
FIG. 4 is a first-order differential curve of FIG. 3.

A first-order differential curve shown in FIG. 4 is obtained by differentiating FIG. 3, the time corresponding to the peak of the curve is marked as $t_{apst}$, and the relationship between the peak time and the measured object thickness or the defect depth is the formula (4). When the thermal diffusivity coefficient α is known, using the formula (4), the thickness or the defect depth can be directly calculated by calculating $t_{apst}$.

When the thermal diffusivity coefficient is unknown, the linear relationship between $t_{apst}$ and the square of the thickness or the defect depth L of the measured object are used. And the linear relationship of a standard sample is obtained via the standard sample. And thus the measured object thickness or the defect depth is obtained.

Figure 5:
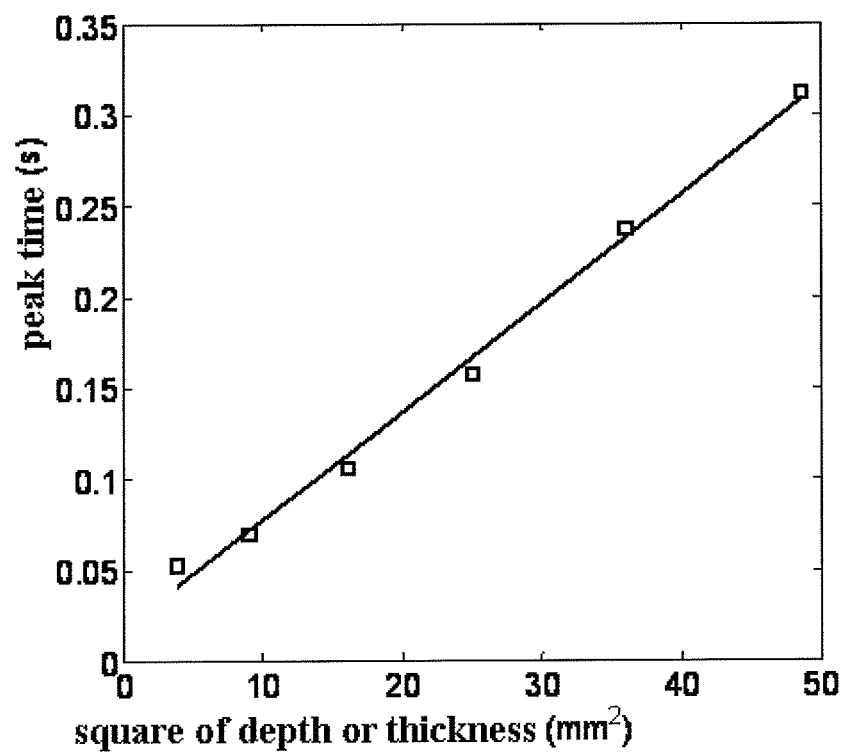
FIG. 5 is a $t_{apst}$ versus $L^2$ curve obtained from an aluminum plate with six wedge-shaped grooves of different depths.

Specifically, a sample which has the same material property with the actual measured object is selected as a standard sample. And then the thermal diffusivity coefficient α of the standard sample is the same as that of the measured object, and the thickness or the defect depth L of the standard sample is known. The standard sample is measured to obtain the $t_{apst}$ of the standard sample, and thus a relationship between $t_{apst}$ and $L^2$ of the standard sample is obtained. For example, by measuring an aluminum plate comprising six wedge-shaped grooves with different depths in the embodiment, a $t_{apst}$ versus $L^2$ curve is obtained as shown in FIG. 5. According to the $t_{apst}$ versus $L^2$ curve and the value $t_{apst}$ obtained by measuring the measured object, a value $L^2$ of the measured object can be then calculated. And thus a value L is obtained.

After processing the thermal image sequence by the method provided by the present subject matter, the thickness or the defect depth of the measured object can be measured without a reference curve and only with a first-order differential.

Specifically, the technological solution employed by the present subject matter comprises the following steps or operations:

1. Heating a measured object by a pulsed heating device, and at the same time, obtaining a thermal image sequence on the surface of the measured object by an infrared thermal imager, and storing the thermal image sequence in a general-purpose memory;

2. Multiplying a temperature-time curve of each pixel in the thermal image sequence by $\sqrt{t}$ of a corresponding time t, thereby obtaining a new curve f;

3. Calculating a first-order differential for the f to obtain a f', and obtaining a peak time $t_{apst}$ of the f';

4. Calculating $L=\sqrt{2\alpha t_{apst}}$ according to the obtained $t_{apst}$ by a formula $$t_{apst} = \frac{L^2}{2\alpha}.$$

In this solution, the thermal diffusivity coefficient α of the measured object is known. Alternately, the linear relationship between $t_{apst}$ and $L^2$ is used, and a standard sample is used to calibrate the linear relationship between $t_{apst}$ and $L^2$, and thus the thickness can be measured.

The heating device used when exciting the measured object may be high-energy flash lamps or other pulse-type heating devices. The high-energy flash lamps or other pulse-type heating devices should have a shorter pulse acting time. The acquisition frequency of the thermal imaging system should be set higher. And the acquisition time should be set according to the specific material properties of the measured object.

Many other benefits will no doubt become apparent from future application and development of this technology.

All patents, published applications, and articles noted herein are hereby incorporated by reference in their entirety.

The above description of the present subject matter is intended to be illustrative, rather than restrictive, it should be appreciated by those skilled in the art that many modifications, changes or equivalences can be made to the present subject matter within the spirit and scope of the claims, but they all will fall within the protection scope of the present subject matter.

What is claimed is:

1. A method for measuring thickness by using pulsed infrared thermal wave technology, comprising:
   (1) heating a measured object by a pulsed heating device placed near a side of the measured object, at the same time, obtaining a thermal image sequence on the surface of the measured object by an infrared thermal imager placed near said side of the measured object, and storing the thermal image sequence in a general-purpose memory;
   (2) multiplying a temperature-time curve of each pixel in the thermal image sequence by $\sqrt{t}$ of corresponding time t, thereby obtaining a new curve f;
   (3) calculating a first-order differential for the f to obtain a f', and obtaining a peak time $t_{apst}$ of the f'; and
   (4) calculating $L=\sqrt{2\alpha t_{apst}}$ by a formula $$t_{apst} = \frac{L^2}{2\alpha},$$

wherein α is a thermal diffusivity coefficient, and L is the thickness or the defect depth of the measured object.

2. A method for measuring thickness by using pulsed infrared thermal wave technology according to claim 1, wherein the thermal diffusivity coefficient α is known.

3. A method for measuring thickness by using pulsed infrared thermal wave technology according to claim 1, wherein said thermal diffusivity coefficient α is unknown, a sample which has the same material property as the measured object and which has a known thickness or a known defect depth L is selected as a standard sample; the standard sample is measured according to the steps (1)-(3) of claim 1 to obtain the $t_{apst}$ of the standard sample, and thus a linear relationship between $t_{apst}$ and $L^2$ of the standard sample is obtained, and a value L of the measured object is calculated according to the linear relationship and the value $t_{apst}$ of the measured object.

4. A method for measuring thickness by using pulsed infrared thermal wave technology according to claim 1, wherein the pulsed heating device is a high-energy flash lamp.

* * * * *